US00PP24796P3

(12) United States Plant Patent
Scheffers

(10) Patent No.: US PP24,796 P3
(45) Date of Patent: Aug. 19, 2014

(54) ***DRACAENA* PLANT NAMED '2004031C'**

(50) Latin Name: *Dracaena fragrans*
Varietal Denomination: 2004031C

(76) Inventor: Ruud Scheffers, Honselersdijk (NL)

( * ) Notice: Subject to any disclaimer, the term of this patent is extended or adjusted under 35 U.S.C. 154(b) by 142 days.

(21) Appl. No.: 13/506,403

(22) Filed: Apr. 16, 2012

(65) Prior Publication Data

US 2013/0276193 P1 Oct. 17, 2013

(51) Int. Cl.
*A01H 5/00* (2006.01)

(52) U.S. Cl.
USPC ..... Plt./383

(58) Field of Classification Search
CPC ..... A01H 5/12; A01H 5/02
USPC ..... Plt./383
See application file for complete search history.

(56) References Cited

PUBLICATIONS

Naktuinbouw National test guidelines for DUS testing. *Dracaena* L. National protocol: NL/DCN/2, retrieved on Oct. 29, 2013, retrieved from the Internet at <http://www.naktuinbouw.nl/en/topic/national-test-guidelines-dus-testing> 8 pp. total.*

Pluto Upov Plant Variety Database 201303, retrieved on Oct. 29, 2013. Retrieved from the Internet at <https://www3.wipo.int/pluto/user/en/index.jsp> for *Dracaena* 2004031c, 2 pp. total.*

* cited by examiner

*Primary Examiner* — June Hwu
(74) *Attorney, Agent, or Firm* — Cassandra Bright

(57) ABSTRACT

A new and distinct *Dracaena* cultivar named '2004031C' is disclosed, characterized by very small habit as well as short leaves and short internodes. The new variety is a *Dracaena*, typically produced as an ornamental plant.

1 Drawing Sheet

Latin name of the genus and species: *Dracaena fragrans*.
Variety denomination: '2004031C'.

BACKGROUND OF THE INVENTION

The new cultivar is the product of chance discovery. The new variety originated as a naturally occurring single branch mutation of the unpatented *Dracaena fragrans* 'Surprise'. Typically, plants of *Dracaena fragrans* are not branching, however, with pinching, or harvesting of cuttings, branches are produced. The new variety was discovered as a branch mutation occurring in a block of harvested motherstock plants.

The new variety was discovered by the inventor, Ruud A. M. Scheffers, a citizen of the Netherlands, in August of 2002 in a commercial greenhouse belonging to the inventor in Honselersdijk, The Netherlands. After identifying the new variety as a potentially interesting selection, the inventor continued confidential testing and propagation of '2004031C', assessing stability of the unique characteristics of this variety.

Asexual reproduction of the new cultivar '2004031C' was first performed at the commercial greenhouse of the inventor in Honselersdijk, The Netherlands by vegetative cuttings in August of 2002. Access to all plants was restricted, as plants were kept in a locked greenhouse not open to the public. Through subsequent propagation by vegetative cuttings, multiple generations have been reproduced, which have shown that the unique features of this cultivar are stable and reproduced true to type. At the time of filing this application, no plant material of the new variety has been made commercially available.

SUMMARY OF THE INVENTION

The cultivar '2004031C' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of '2004031C'. These characteristics in combination distinguish '2004031C' as a new and distinct *Dracaena* cultivar:

1. Very compact plant.
2. Short leaves.
3. Short internodes.

PARENT COMPARISON

Plants of the new cultivar '2004031C' are similar to the parent, *Dracaena fragrans* 'Surprise' in most horticultural characteristics. The new variety, however, is two to three times smaller at maturity, compared to the parent. Additionally, '2004031C' produces erect leaves compared to the more hanging nature of the parent plant's foliage, as well as solid green leaves, compared to the multi colored foliage of the parent plant.

COMMERCIAL COMPARISON

'2004031C' is similar in most horticultural characteristics to the unpatented variety *Dracaena fragrans* 'Janet Craig Compacta'. The two varieties differ in mature size with '2004031C' reaching a mature size two to three times smaller compared to 'Janet Craig Compacta'.

BRIEF DESCRIPTION OF THE PHOTOGRAPH

The accompanying photograph in FIG. 1 illustrates in full color a typical plant of '2004031C' grown in a commercial greenhouse in Honselersdijk, The Netherlands. This plant is approximately 5 months old, shown planted in a 15 cm. container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe '2004031C' plants grown in a greenhouse in Honselersdijk, The Netherlands. A steady temperature of approximately 20° C. at night and 20° C. during the day was maintained. No artificial light, photoperiodic treatments were given to the plants. Measurements and numerical values represent averages of typical plant types.

Botanical classification: *Dracaena fragrans* '2004031C'.

PROPAGATION

Time to initiate rooting: About 4 weeks at approximately 20° C. 6 weeks for full rooting.

Root description: Moderately thick, moderately fibrous, not fleshy, young roots Yellow-White 158D, older roots Greyed-Orange 163D.

PLANT

Age of plant described: 5 months.

Pot size of plant described: 15 cm. pot.

Growth habit: Broad upright.

Height: Approximately 17.9 cm.

Plant spread: Approximately 11.6 cm.

Growth rate: Slow, approximately 3 cm per month.

Branching characteristics: Not free branching, growing with one main stem from the base, will only develop lateral branches after pinching/pruning.

Diameter of stem: Approximately 0.8 cm. Stem not visible but fully covered by leaves, individual stem characteristics outside of diameter are not measurable.

Internode length: Average 0.2 cm.

Texture of stem: Stem not visible but fully covered by leaves.

Color of stem: Stem not visible but fully covered by leaves.

Stem strength: Very strong.

Number of leaves per stem: Average 60.

FOLIAGE

Leaf:

*Arrangement*.—Alternate (spirally).

*Average length*.—Approximately 7.7 cm.

*Average width*.—Approximately 2.2 cm.

*Shape of blade*.—Lorate.

*Aspect*.—Average angle at base: 40°, tips curved to near horizontal) (90°). 0°=vertical.

*Apex*.—Narrow acuminate, not sharp, twisted.

*Base*.—Broad cuneate.

*Attachment*.—Sheathing.

*Margin*.—Entire, slightly undulate.

*Texture of top surface*.—Smooth, very glossy.

*Texture of bottom surface*.—Smooth, moderately glossy.

*Color*.—Young foliage upper side: Near RHS Yellow-Green N144A, tip darker; Green N137A. Young foliage under side: Near RHS Green 143C, tip darker; Yellow-Green 146B. Mature foliage upper side: Near RHS Green N137A. Mature foliage under side: Near RHS Yellow-Green 146A.

*Venation*.—Type: Parallel. Color: Upperside: As leaf blade. Underside: As leaf blade.

Sheath:

*Average length*.—Approximately 0.8 cm.

*Average width*.—Approximately 0.3 cm.

*Color*.—Near RHS Green-White 157D, margins near 157B.

*Texture*.—Smooth, glossy.

OTHER CHARACTERISTICS

Flower production: Not observed.

Disease and pest resistance: Neither resistance nor susceptibility to normal diseases and pests of *Dracaena* has been observed.

Drought tolerance and temperature tolerance: Moderately high drought resistance, good heat resistance.

Fruit/seed production: Not observed.

What is claimed is:

1. A new and distinct cultivar of *Dracaena* plant named '2004031C' as herein illustrated and described.

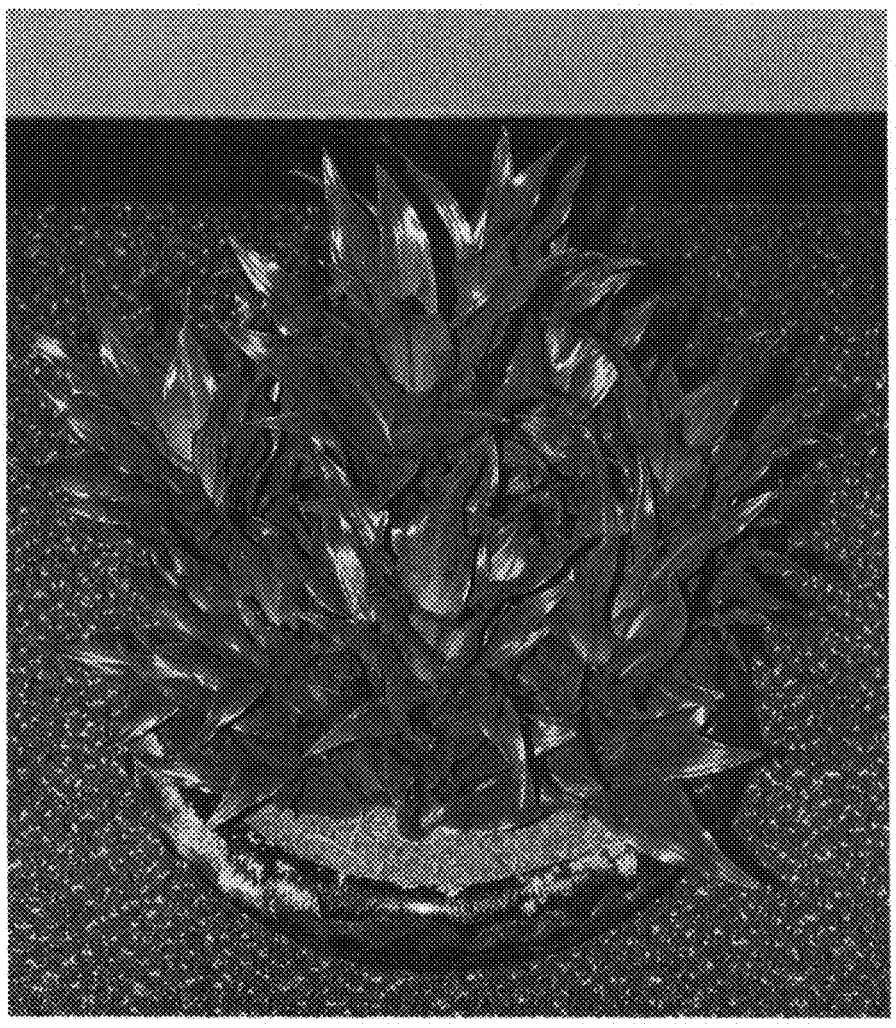

* * * * *